US 6,575,974 B2

(12) United States Patent
Gotfried (10) Patent No.: US 6,575,974 B2
(45) Date of Patent: Jun. 10, 2003

(54) SURGICAL DEVICE AND METHOD FOR CONNECTION OF FRACTURED BONES

(76) Inventor: Yechiel Gotfried, 10, Ben-Gurton Ave., 27000 Kiriat Blalik (IL)

( * ) Notice: Subject to any disclaimer, the term of this patent is extended or adjusted under 35 U.S.C. 154(b) by 0 days.

(21) Appl. No.: 09/916,400

(22) Filed: Jul. 26, 2001

(65) Prior Publication Data

US 2003/0023246 A1 Jan. 30, 2003

(51) Int. Cl.[7] ............................................... A61B 17/56
(52) U.S. Cl. .......................................... 606/67; 606/72
(58) Field of Search ............................. 606/65, 69, 72, 606/73, 86, 96, 67; 411/383, 410

(56) References Cited

U.S. PATENT DOCUMENTS

| 4,465,065 | A | * | 8/1984 | Gotfried | 606/65 |
|---|---|---|---|---|---|
| 4,940,467 | A | * | 7/1990 | Tronzo | 606/66 |
| 5,176,681 | A | * | 1/1993 | Lawes et al. | 606/64 |
| 5,429,641 | A | * | 7/1995 | Gotfried | 606/67 |
| 5,644,889 | A | * | 7/1997 | Getz | 52/713 |
| 5,741,266 | A | * | 4/1998 | Moran et al. | 606/96 |
| 5,895,390 | A | * | 4/1999 | Moran et al. | 606/96 |
| 6,001,103 | A | * | 12/1999 | Hitomi et al. | 606/73 |
| 6,183,477 | B1 | * | 2/2001 | Pepper | 606/104 |
| 6,221,074 | B1 | * | 4/2001 | Cole et al. | 606/62 |
| 6,261,290 | B1 | * | 7/2001 | Friedl | 606/64 |
| 6,379,364 | B1 | * | 4/2002 | Brace et al. | 606/96 |

* cited by examiner

Primary Examiner—Kevin T. Truong
Assistant Examiner—Victor X Nguyen
(74) Attorney, Agent, or Firm—Frishauf, Holtz, Goodman & Chick, P.C.

(57) ABSTRACT

A screwdriver for re-joining first and second pieces of a fractured bone in cooperation with a connector plate. A screw has an screw-shaped inner end for biting into the bone upon passing through a bore of the connector plate, and out of a hole in the first bone piece. The screwdriver includes a first shaft unit to engage and rotate the screw to move the screw axially, and a second shaft unit to rotate an axially movable sleeve. Axial movement of the first shaft unit moves the screw so that the outer end of the screw passes through the sleeve and into the second shaft unit such that the inner end of the screw protrudes inwardly from an inner end of the sleeve, whereby a threaded outer end of the sleeve is engaged with the bore of the connector plate before the screw is driven into the bone.

58 Claims, 7 Drawing Sheets

SURGICAL DEVICE AND METHOD FOR CONNECTION OF FRACTURED BONES

FIELD OF THE INVENTION

The present invention is a surgical device for setting fractured bones, such as connecting the fractured neck of a femur bone to its shaft with screws by means of a pre-drilled connector plate, without requiring a large incision to be made in the overlying skin and tissue. In particular, a new screwdriver is provided, together with a technique for its use, that improve the ease and reliability with which the screws are inserted and the fractured bone set.

BACKGROUND OF THE INVENTION

The present invention is an improvement of my U.S. Pat. Nos. 4,465,065 and 5,429,641. The subject matter of both patents is hereby incorporated by reference. Only those features of both patents are summarized below as are deemed helpful in explaining the structure, operation, need for and advantages of the present invention. A complete and thorough explanation of all the features of those patents can be gained, of course, from a direct reading thereof.

In U.S. Pat. No. 4,465,065 the connector plate has a sharp lower edge by which it penetrates through a small incision in the trochanter region into close contact with the shaft. During the operation the plate is temporarily attached to the horizontal portion of a connector arm, while the vertical portion of the connector arm extends parallel to the connector plate and is provided with holes which are coaxial with the holes in the plate. Concentric inner and outer guide tubes are inserted through the holes in the vertical portion of the connector arm, are pushed through the soft tissue up to the plate and serve as guides for pre-drilling of the bone parts in the correct position as viewed by X-ray equipment. After such pre-drilling, the inner guide tubes are removed and the outer tubes serve for guiding the insertion of long screws, and are afterwards removed. The long screws are tightened so as to compress the fracture. The plate is secured to the femur shaft with short screws, and the connector arm is then detached from the plate, and the wound is closed.

The device disclosed in U.S. Pat. No. 5,429,641 serves the same purpose as and has many features in common with the above-described device, but is designed to avoid certain of its drawbacks which came to light during its use in surgical operations ("operations" hereinafter) of the kind referred to.

In particular, U.S. Pat. No. 5,429,641 discloses a screw-and-sleeve assembly in which each long screw is axially movable within an associated sleeve that has a screw-threaded end that is firmly connected to a threaded bore in the connector plate. This feature permits active compression of the fracture by the surgeon and avoids a drawback of the above-described invention involving a gradual protrusion of the screw heads into the soft tissue causing subsequent irritation and pain to the patient.

Before going into its constructional details, it should be noted that the following directional expressions will be employed in respect of the femur bone, the connector plate, the screws and the related components of the surgical device. The expressions "top" and "upper portion" of any part will refer to the femur top, and the "bottom" or "lower portion" will refer to the direction towards the knee joint. The expression "inside" or "inner" will refer to parts close to the bone or pointing towards it, while the expression "outside" or "outer" will refer to those parts which are outside the human body being operated on, or pointing away from the bone.

The surgical device of U.S. Pat. No. 5,429,641 includes the following components.

Components Which are to Remain in the Body After the Operation is Completed:
  1. A connector plate I.
  2. Two long screws II used for connecting the fractured parts to the connector plate.
  3. Two or more short screws 33 securing the lower plate portion to the femur shaft.
B. Auxiliary Equipment for Insertion and Fixation of the Permanent Components:
  1. An angular connector arm IV.
  2. Two long inner and outer guide tubes of a length sufficient to extend from the bores in the connector arm to the corresponding oblique bores in the connector plate. Outer guide tube 31 has an inner diameter corresponding to the diameter of the screw to be inserted and to be screwed into the fractured bone. Two inner, removable and alternately insertable guide tubes, are provided. Tube 32 is used first. It is concentrically bored to the diameter of a guide wire 30 to be pushed therethrough into the bone. After tube 32 has served its purpose and is removed, second tube 32a is used. It is concentrically bored to the diameter of a drill bit 35 adapted to pre-drill the femur bone for reception of the two screw-and-sleeve assemblies which include the long screws. The diameter of the pre-drilled bore in the femur accommodates the sleeve therein.
  3. Two or more shorter guide tubes (not shown) for pre-drilling bone before final insertion of the short screws for firm attachment of the connector plate to the femur shaft.
  4. A special screwdriver V adapted for manipulating the long screws and their sleeves to fix the sleeves to the connector plate, to insert the screws into the fractured bone, and to compress the fracture.

The auxiliary equipment is removed from the body after the connector plate has been firmly connected to the femur shaft with the short screws and long screws, and the fracture has been connected and duly compressed by means of the long screws, whereafter the wounds are to be dressed.

Figure 1:
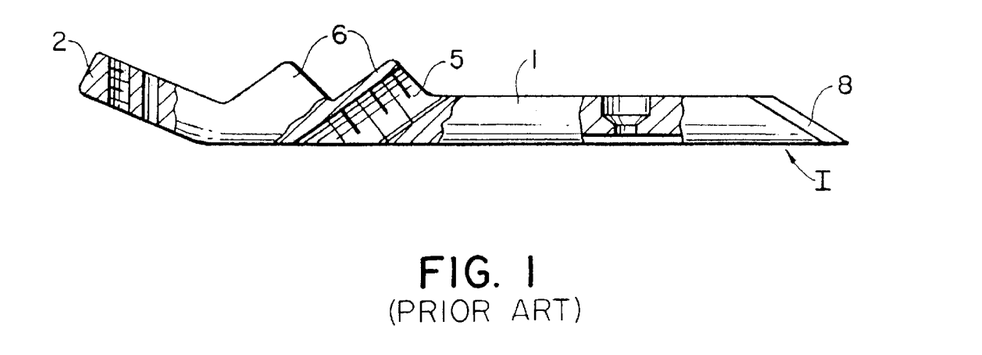
FIG. 1 is a side view and partial sectional view of a prior art connector plate.

The connector plate I of substantially rectangular cross section illustrated in FIG. 1 includes a straight lower, main portion 1 and a head portion 2 outwardly bent in respect of the main portion, to conform to the contour of the bone. Next to the head portion, two obliquely-directed, screw-threaded bores 5 penetrate the main portion at an angle of about 130°, the outer surface of the main portion being thickened by two lugs 6 permitting a greater length of the bores 5. The lower end 8 of the main portion is sharpened for the purpose of penetrating through the soft tissue and muscles close to the femur shaft during insertion of the connector plate through a small cut in the skin into its final position where it is attached to the bone with short screws.

Figure 2:
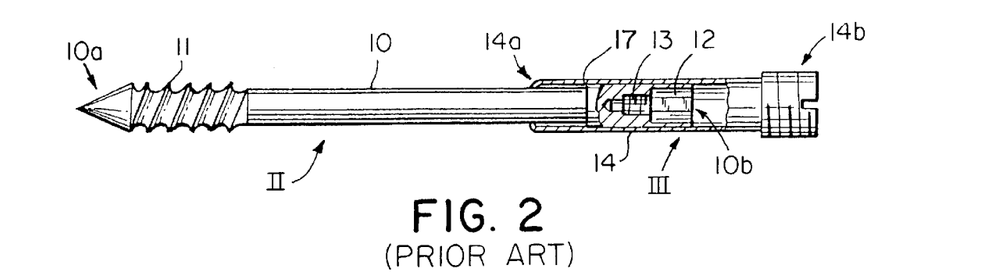
FIG. 2 is a side view and partial sectional view of the long screw positioned in the sleeve of FIG. 4, as in the prior art.
Figure 3:
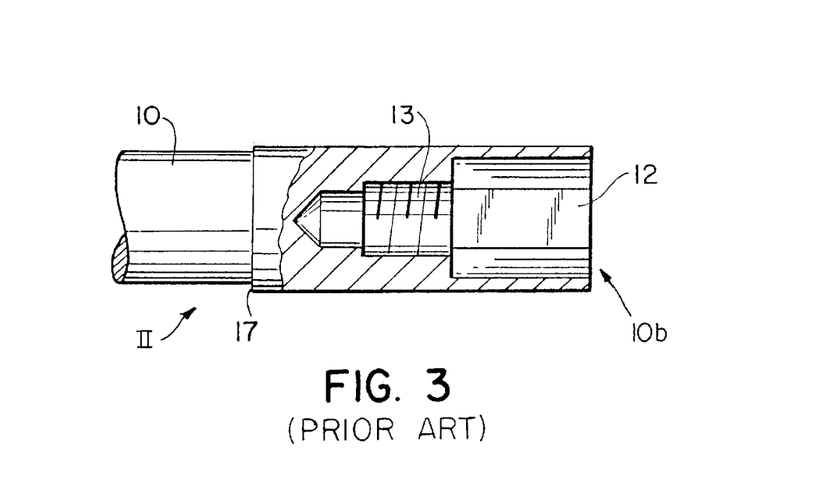
FIG. 3 is a sectional view through the outer end of the prior art screw illustrated in FIG. 2.
Figure 4:
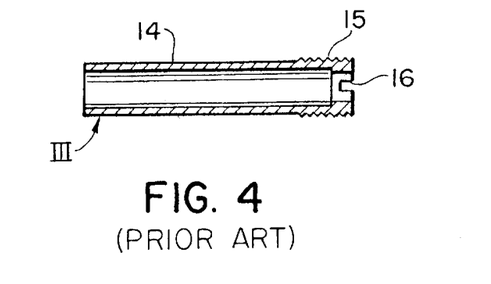
FIG. 4 is a longitudinal sectional view of the prior art sleeve shown in FIG. 2.

An assembly of a long screw II and its relatively short sleeve III is illustrated in FIG. 2, and details of both are shown in FIGS. 3 and 4. The screw includes a relatively long shaft 10, an inner end 10a provided with screw thread 11 similar to that provided on wood screws, and an outer end 10b having a coaxial recess 12 formed therein in the shape of a hexagon that is axially extended with a screw-threaded bore 13 of a smaller diameter. The outer end 10b of the screw is slidably, but firmly, movable lengthwise and rotatably within the inner bore of sleeve body 14, which has its outer end 14b provided with outside screw thread 15 and slotted by two or four slots 16 serving to engage the screwdriver V. The inner end 14a of the sleeve III is inwardly crimped slightly, thereby preventing the screw II from sliding out of the sleeve by contact with a step 17 on the screw shaft.

FIGS. 5–10 illustrate the auxiliary equipment serving for inserting and tightening long screws II and for compressing the fracture by bringing the bone parts toward each other after insertion of the screws is completed. The main component is an L-shaped connector arm IV which includes a horizontal portion 20 and a vertical portion 21 firmly connected to each other at right angles. The vertical portion 21 contains two large, obliquely-directed bores 26 which are coaxially aligned with the bores 5 in the connector plate, but are of a larger diameter for permitting the passage and fixation of the guide tubes.

Figure 5:
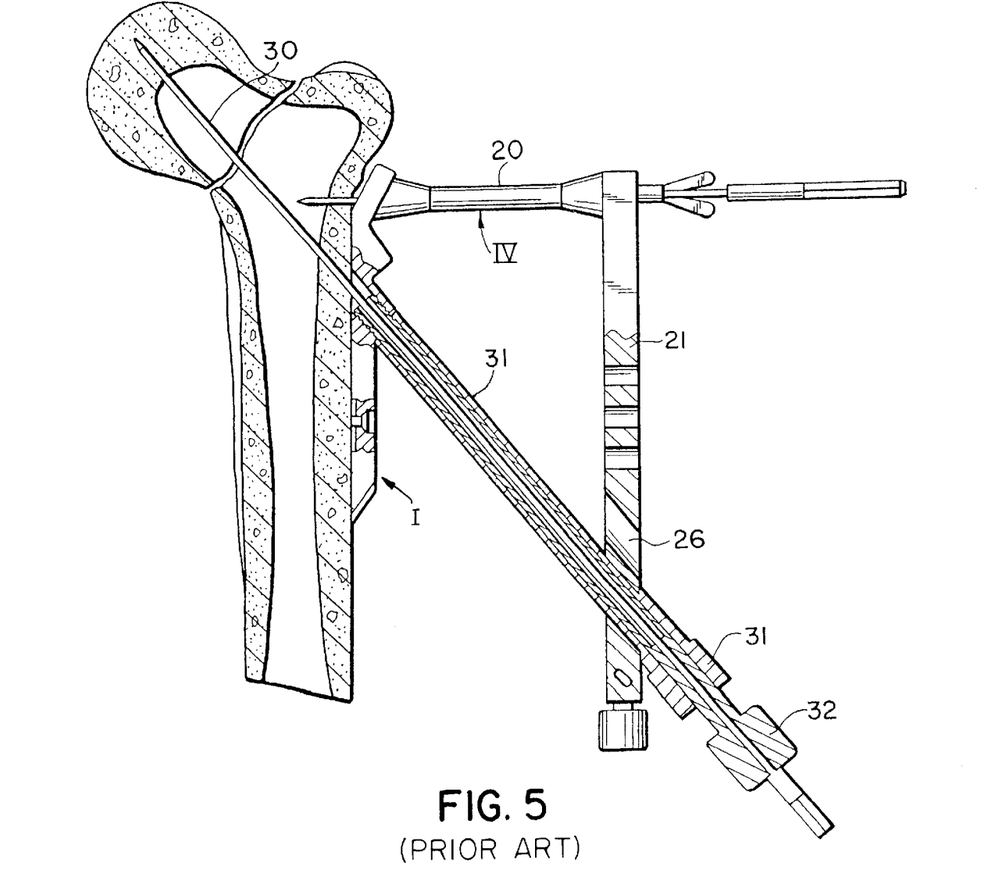
FIG. 5 is a sectional view of the connector plate, the connector arm and auxiliary equipment, including a first guide tube, at the beginning of an operation, as in the prior art.

FIG. 5 illustrates an early stage of a surgical operation performed with the above-described device. After the connector plate I has been manually inserted by the surgeon into the thigh through a small cut and has been slid into an approximate position while being viewed by means of X-ray equipment, its correct and precise location in relation to the neck of the femur is found by means of a guide wire 30 which is inserted into the bone of the femur upper shaft and into the bone of the femur neck through inner guide tube 32 located within outer tube 31 extending from the bore 26 of the connector arm to the screw-threaded bore 5 of the connector plate. The tip of guide wire 30 is a diamond bit, and the guide wire is rotated by a handheld type of power tool (not shown) which is well known and, thus, its details are not deemed necessary.

The inner guide tube 32 is screwed into bore 5 of the plate in order to permit exact centering of guide wire 30 and to prevent its inadvertent disengagement from the connector plate. In case connector plate I is not yet in the correct location, the guide wire 30 is withdrawn, the connector plate is moved by means of the connector arm into another position and the guide wire 30 is again inserted into the bone. If the location is found to be correct as seen on an X-ray image, the connector plate is fixed to the bone in this position, whereupon the guide wire 30 and the inner tubular guide (32) are removed. Outer tube 31 is meanwhile held in place by a set screw (not shown in FIG. 5 but identified as 28 in FIG. 9 of U.S. Pat. No. 5,429,641). Then, inner guide tube 32 is replaced within outer tube 31 by the second inner guide tube 32a having a wider inner bore than tube 32 (see FIG. 7), in order to accommodate drill bit 35 which is inserted therethrough for the purpose of pre-drilling the bone prior to use of the long screws.

With a mechanical rotation of drill bit 35 by the above-mentioned power tool, a hole is drilled through the upper femur shaft and into the lower part, or base, of the neck for subsequent insertion thereinto of a long screw. Such pre-drilling provides room in the bone to (as explained below in connection with subsequent steps) receive sleeve III while the threaded tip of the long screw, which is self-cutting, drills its way into the bone without pre-drilling. Since the diameter of drill bit 35 is preferably smaller than the diameter of sleeve III, the pre-drilling is done in two stages, with use of drill bit 35 being followed by another drill bit (not shown) having a diameter corresponding to that of sleeve III.

Figure 8:
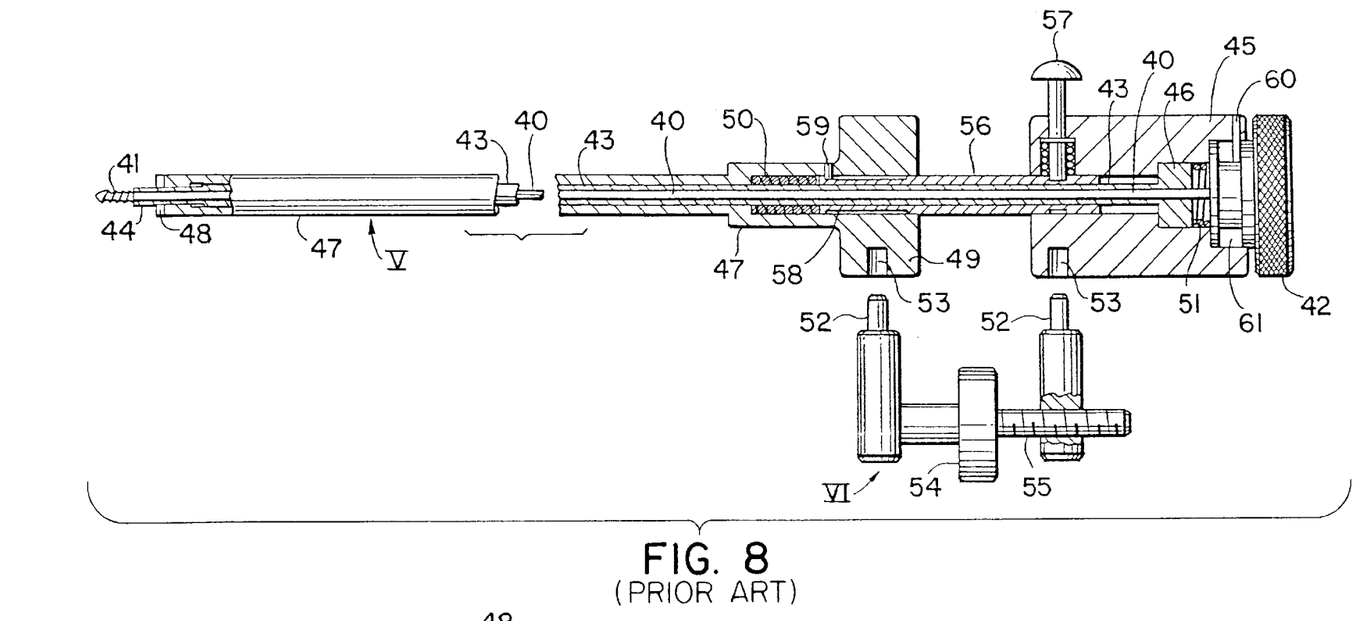
FIG. 8 is a longitudinal section through the screwdriver used in manipulating a long screw and its sleeve, as in the prior art.
Figure 9:
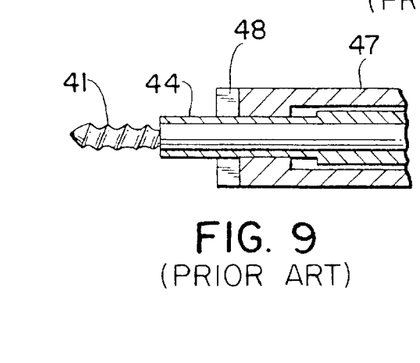
FIG. 9 is an enlarged section of the left hand end of the screwdriver shown in FIG. 8.
Figure 10:
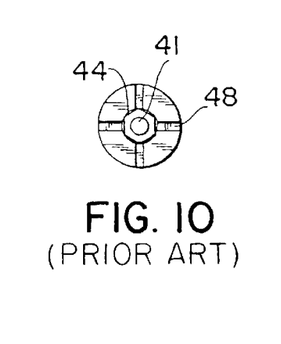
FIG. 10 is a side view of the screwdriver taken from the left side as shown in FIG. 8.

The screwdriver V is illustrated in FIGS. 8–10. It comprises the following three concentrically aligned shafts which are independently movable in both axial and rotary directions:

1. An innermost shaft 40 has a screw-threaded end 41 suitable for engaging the bore 13 in the outer end 10b of the long screw II. Shaft 40 is rotatable and longitudinally movable by a handle 42 at the outer end of the screw driver.

2. An intermediate tubular shaft 43 has a hexagon-shaped inner end 44 adapted for driving engagement with the hexagonal-shaped recess 12 in the long screw II. Rotation of shaft 43 is used to drive the screw into the pre-drilled bone. Shaft 43 is rotated by cylindrical handle 45 coupled thereto via a disc 46 firmly mounted on the shaft 43.

3. An outermost tubular shaft 47 has an inner end in the form of cross-wise aligned edges 48 for engagement with slots 16 in the sleeve III. Shaft 47 is rotatable by means of a cylindrical handle 49 for the purpose of screwing sleeves III into the connector plate I.

An outer sleeve 56 is rotationally and longitudinally movable on the intermediate shaft 43. Sleeve 56 is provided with a circumferential recess 58 engaged by a pin 59 serving to limit the longitudinal motion of shaft 47. A second circumferential recess (unnumbered) is provided at the other end of sleeve 56 and engages a stop 57.

The above-described components can be axially moved relative to each other, but are urged into their normal position by helical springs 50 and 51. Additional axial motion of the tubular shaft 43 is made possible by withdrawal of stop 57 from its associated recess for a specific use that will be explained below.

Figure 6:
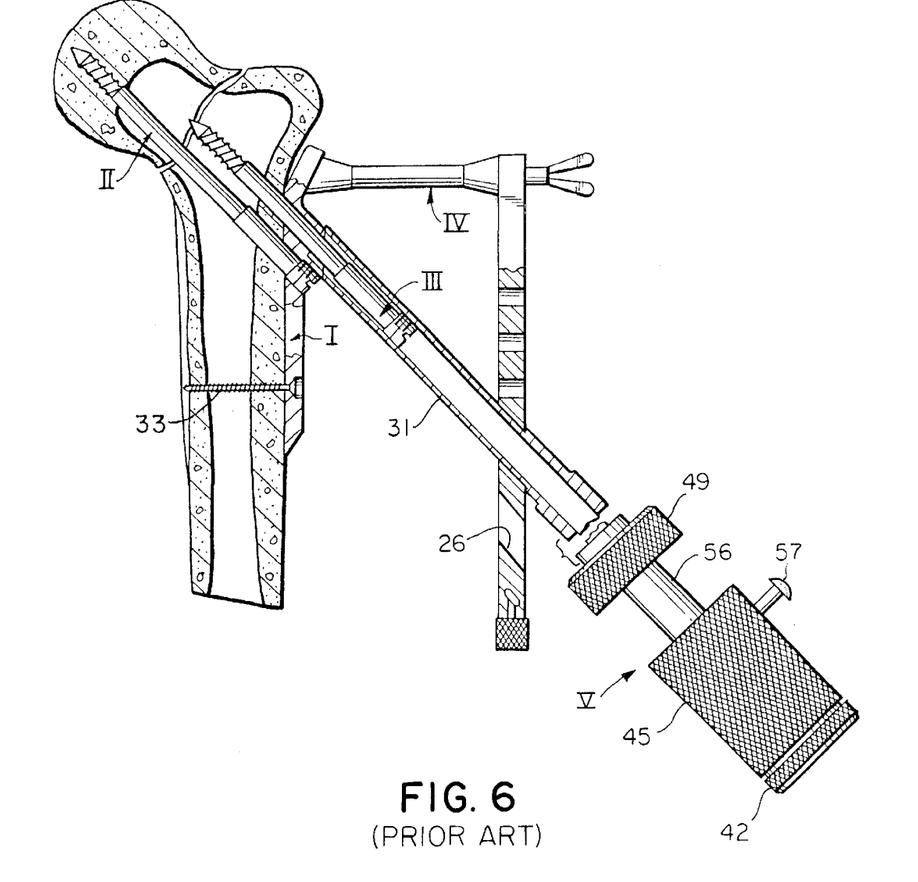
FIG. 6 is a sectional view of the connector plate, the connector arm, and the screwdriver (shown in FIG. 8), showing a later stage of the operation, with one long screw and sleeve in final position and a second screw on its way to its final position, as in the prior art.
Figure 7:
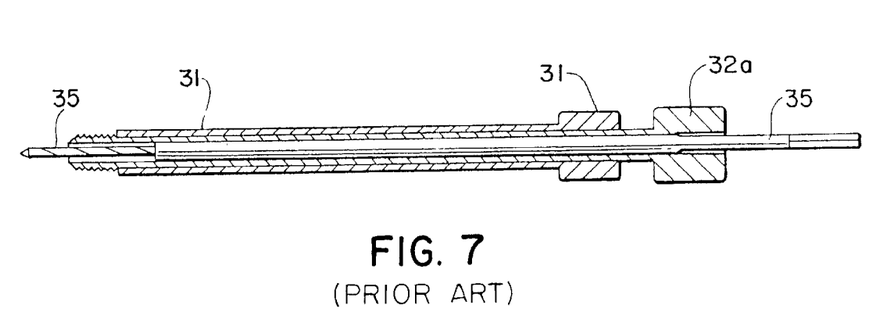
FIG. 7 is a longitudinal sectional view of a second removable guide tube and a drill bit inserted therein, as in the prior art.

After the bone has been pre-drilled in alignment with the oblique bores 26, the inner tubular guide 32a is removed. Then, as illustrated in FIG. 6, the two screw-and-sleeve assemblies are inserted and fastened, one after the other, with the aid of the screw driver V, as follows. A long screw II is retracted into its sleeve III and positioned so that its outer end 10b can be engaged by screwdriver V. The hexagon-shaped end 44 of the screwdriver is pushed into the correspondingly shaped recess 12 in the outer end 10b of the screw. By rotating handle 42 and pushing it against the force of helical spring 51, the threaded end 41 of the innermost shaft 40 of the screw-driver is screwed into screw-threaded bore 13 of the screw, while the protruding edges 48 of the outermost tubular shaft 47 are urged into slots 16 in the end of sleeve III by means of helical spring 50. Additional tightening of the threaded end 41 into bore 13 connects and firmly secures the screw-and-sleeve assembly to the screw-driver V.

By means of the screwdriver V, the screw-and-sleeve assembly is pushed in an inward direction through the outer tubular guide 31, and rotated as far as the screw-thread 15 on the sleeve III allows. With rotation of handle 49 the sleeve is screwed into bore 5 of the connector plate. By pulling out the stop 57, handle 45 which is connected to the inner shaft 43 by means of collar 46, can be moved in an inward direction thereby pushing shaft 43 inwardly. By rotating and pushing handle 45 inwardly, screw II is moved relative to sleeve III. More specifically, the outer end 10b travels within sleeve body 14 as threaded inner end 10a and shaft 10 extend therefrom while being urged through the femoral neck into the head portion. The threaded inner end 10a enters into the pre-drilled bore in the femur bone and continues being screwed more deeply thereinto as handle 45 is turned manually by the surgeon.

Rotation of handle 45 is stopped as soon as the screw II has reached the required depth in the femur head as viewed by X-ray equipment, or whenever step 17 on the screw has reached the crimped inner end 14a of the sleeve (see FIG. 2). A pin 60 engaged within a circumferential groove 61 limits the distance to which handle 42 can be moved in an outward direction, while being urged there by spring 51. In addition, during fracture compression (as explained below) pin 60 transfers the load from handle 45 to shaft 40 via handle 42.

In order to pull the fractured head in the direction of the femur shaft and, thus, to compress the fracture, a retracting device VI is attached to the handles 45 and 49 of screwdriver V by means of pins 52 inserted into corresponding holes 53. By rotating the handwheel 54, screw 55 pulls handles 49 and 45 apart. Since the position of handle 49 is fixed relative to the connector plate, this produces outward motion of handle 45. Such outward motion of handle 45 is transferred to handle 42 (by means of pin 60), thereby pulling (via shaft 40) the attached screw II (via threaded end 41 screwed into hole 13) outwardly and into the sleeve III which is firmly screwed and secured to the connector plate. Opposing surfaces at the fracture site have interdigitating spikes which engage when the fracture is sufficiently compressed. This maintains the compression even after the pull created by the screwdriver is released. Muscle pull and weight-bearing also help to maintain this compression. After insertion and fixation of the first screw, the second screw is inserted into the fractured bone parts in the same manner.

With insertion of both long screws as described above, and also of the short screws, the connector plate I is firmly attached to the femur shaft. The connector arm is then removed from the plate and out of the body, the skin incisions are closed, and the wounds are dressed.

A disadvantage of the surgical device disclosed in U.S. Pat. No. 5,429,641 arises from the fact that the screw-and-sleeve assembly is moved through guide tube 31 while outer end 10b of long screw II is at outer end 14b of sleeve III. Since screw II is considerably longer than sleeve III, the threaded tip at inner end 10a of screw II will initially bite into the bone (beyond the pre-drilled bore in the femur) before thread 15 of sleeve III threadedly engages tapped bore 5. Any minute deflection of screw II from perfect alignment will prevent thread 15 from engaging tapped bore 5. For example, the longest contemplated length for screw II is 118 mm and the length of sleeve III is 42 mm. In order for the threaded portion 15 of sleeve III to reach bore 5, it is necessary for the tip of screw II to bite into the bone by a distance of up to 82 mm. It has been found in practice that despite the precise alignment achieved by the pre-drilling operation as described above, when screw II bites into the bone, certain minute lateral deflections from the perfect alignment can occur. Even such minute deflections can prevent the threaded portion 15 on sleeve III from threadedly engaging tapped bore 5. If this occurs, then it becomes impossible to secure sleeve III to connector plate I. This may result in loosening sleeve III outwardly into the soft tissue.

Such a situation is not tolerable. Consequently, the surgeon must reposition the device by repeating the above-described steps until the correct path is found. This is time consuming and prolongs the surgical operation.

SUMMARY OF THE INVENTION

One object of the present invention is to provide a surgical device for setting bones that avoids the possibility of a misalignment which prevents engagement between threaded portion 15 of sleeve III and tapped bore 5 of connector plate I.

Another object of the present invention is to simplify the special screwdriver for easier surgical use and cleaning.

A further object of the present invention is to reduce the manufacturing cost of the special screwdriver.

These and other objects are attained in accordance with one aspect of the present invention directed to an improved screwdriver for use as part of auxiliary equipment serving to insert and connect a surgical device for percutaneous connection of a fractured upper part of a femur to a femur shaft of a patient, wherein the surgical device comprises the following components to remain in the body of the patient:

(a) a bar-shaped plate having an axis, an inner surface to be placed onto the femur, an outer surface, a head portion and a bottom provided with a sharpened end for insertion of the bar-shaped plate through a small incision in the skin of the patient, the bar-shaped plate being provided in a lower portion thereof with at least two countersunk, through-going bores and in an upper portion thereof with two adjoining oblique, screw-threaded bores directed in an upward direction at an angle of about 130°, a screw-threaded bore perpendicular to the axis of the bar-shaped plate being provided in the head portion, (b) two long screws, each screw having a straight shaft, a wood-screw-shaped inner end for insertion into the fractured upper part of the femur and an outer end coaxially recessed with a polygonal shape, the recess being continued by a screw-threaded bore concentric with an axis of the shaft, (c) a sleeve of a shorter length than the screw, with the outer end of the screw being positioned in the sleeve in a manner so as to be movable in both axial and rotational directions in the sleeve, the sleeve having an outer end provided with a screw-thread corresponding to the screw thread in the oblique bores in the bar-shaped plate such that the sleeve is threadedly engageable within the oblique bores, the sleeve further having at least two recesses for engagement of a screwdriver, and (d) at least two shorter screws for securing the bar-shaped plate to the femur shaft, the at least two shorter screws extending through the countersunk, through-going bores into bone material of the femur shaft. The auxiliary equipment comprises: (a) an angular connector arm including a short horizontal portion for connection to the head portion of the bar-shaped plate and a longer vertical portion extending parallel to the lower portion of the bar-shaped plate, wherein the horizontal portion is provided with an axial perforation for passage of a screw engaging with the screw-threaded bore in the head portion of the bar-shaped plate and is shaped to conform to the shape of the head portion to ensure absolute parallelism of the vertical portion with the bar-shaped plate, and wherein the vertical portion is provided with two adjoining obliquely directed bores coaxially aligned with the two oblique screw-threaded bores in the plate, and with at least two straight bores coaxially aligned with the at least two countersunk, through-going bores in the plate, (b) a first tubular guide of an outer diameter cooperating with the oblique bores in the angular connector arm and of an inner diameter corresponding to an outer diameter of the sleeve covering the long screw, of a length compatible with a distance between the respective oblique bores in the plate and the angular connector arm, (c) a first removable tube for insertion into the first tubular guide and having a bore with an inner diameter corresponding to an outer diameter of a guide wire to be pushed therethrough into the fractured upper part, (d) a second removable tube for insertion into the first tubular guide and having a bore with an inner diameter corresponding to a diameter of a drill to provide a pre-drilled portion of the femur sized to accommodate the sleeve therein; (e) a guide wire to be pushed through the bore in the first removable tube, (f) a drill to be inserted into the bone material through the bore in the second removable tube, (g) a second tubular guide for insertion into the straight bores in the angular connector arm, of a length compatible with the distance to the bar-shaped plate, and of an inner diameter corresponding to an outer diameter of the shorter screws, and (h) a screwdriver for insertion and fixation of the long screws. The screwdriver includes: (a) an inner shaft provided with a screw-threaded inner end for engagement with the screw-threaded bore in the recessed end of the long screw, (b) an intermediate shaft provided with a polygonal inner end for engagement with the polygonal recess in the long screw to drive the long screw into the upper part of the femur by applying rotational and inwardly directed forces so that the wood-screw shaped inner end bites into the upper part of the femur, and (c) an outer shaft provided at an inner end thereof with protruding teeth for engagement with the recesses in the sleeve, wherein the screwdriver is provided with means for pulling the long screw in an outward direction relative to the sleeve, all of the inner, intermediate and outer shafts being independently movable in both axial and rotational directions by handles attached to outer ends thereof, and resilient components are provided to adjust axial alignment of the respective shafts relative to each other.

The improvement in the screwdriver comprises: (a) force-applying means for pulling a section of the long screw by the inner shaft engaged therewith into the outer shaft to have only a length of the long screw protruding inwardly of the sleeve such that the screw-thread on the outer end of the sleeve can be threadedly engaged with each one of the screw-threaded oblique bores in the connector plate before the inner end of the long screw is driven to bite into the femur past the pre-drilled portion, and (b) means in the outer shaft to accommodate therein the section of the long screw.

In accordance with another aspect of the present invention, an improved screwdriver is provided which is used during surgery for re-joining two pieces of a fractured bone in cooperation with a connector plate adapted to be secured to a first one of the two bone pieces. The connector plate has at least one screw-threaded bore with its axis being directed at a second of the bone pieces through a pre-drilled portion of the first bone piece. A screw is provided having a screw-shaped inner end for, as the screw is driven with forceful rotation, initially biting into the bone upon passing through the bore of the connector plate and out of the pre-drilled portion of the first bone piece, the screw having an outer end adapted to be engaged with the screwdriver. A sleeve is provided of a shorter length than the screw which is axially movable and rotatable on the screw, the sleeve having an outer end provided with a screw thread corresponding to the screw thread in the bore of the connector plate for threaded engagement therewith. The screwdriver comprises: a first shaft unit with engaging means at its inner end for engaging the first shaft unit with the screw to move the screw axially and to rotate the screw; a second shaft unit axially movable and rotatable relative to the first shaft unit and having rotation means at its inner end for rotating the sleeve; and motive means for effecting axial movement of the first shaft unit for moving the screw engaged therewith outward relative to the sleeve so that the outer end of the screw passes through the sleeve and into the second shaft unit to a position therein such that the inner end of the screw protrudes inwardly from the inner end of the sleeve by a length such that the threaded outer end of the sleeve can be threadedly engaged with the bore of the connector plate before the screw is driven to have the inner end of the screw initially bite into the bone beyond the pre-drilled portion.

Yet another aspect of the present invention is directed to an improved screwdriver used during surgery for re-joining two pieces of a fractured bone in cooperation with the above-described connector plate, and screw-and-sleeve assembly. The screwdriver comprises: a first shaft unit having a screw-threaded tip at its inner end corresponding to a screw-threaded bore in the screw for threaded engagement therewith, the first shaft unit further comprising a polygon-shaped portion at its inner end corresponding to and drivingly engageable in a polygon-shaped recess in the screw; a second shaft unit axially movable and rotatable relative to the first shaft unit and having a transverse edge at its inner end corresponding to and drivingly engageable in a slot on the outer end of the sleeve; a first handle unit attached to the outer end of the first shaft unit, the first handle unit being coupled to the screw as the screw-threaded tip of the first shaft unit is threadedly engaged in the screw-threaded bore of the screw, whereby the screw is movable axially with axial movement of the first handle unit, and whereby the screw is rotatable with rotational motion of the first handle unit; and a second handle unit attached to the outer end of the second shaft unit, the second handle unit being coupled to the sleeve as the transverse edge at the inner end of the second shaft unit is positioned within the slot on the outer end of the sleeve, whereby the sleeve is rotatable and axially movable with respective rotation and axial motion of the second handle unit; the second shaft unit being sized to accommodate therein a portion of the screw which is defined by moving the screw outward relative to the sleeve so that the outer end of the screw passes through the sleeve and into the second shaft unit to a position therein such that the inner end of the screw protrudes inwardly from the inner end of the sleeve by only a length such that the threaded outer end of the sleeve can be threadedly engaged with the bore of the connector plate before the screw is driven to have the inner end of the screw initially bite into the bone beyond the pre-drilled portion.

One further aspect of the present invention is directed to an improved screwdriver used during surgery for re-joining two pieces of a fractured bone in cooperation with the above-described connector plate, and screw-and-sleeve assembly. The screwdriver comprises: a first shaft unit having a screw-threaded tip at its inner end corresponding to a screw-threaded bore in the screw for threaded engagement therewith, the first shaft unit further comprising a polygon-shaped portion at its inner end corresponding to and drivingly engageable in a polygon-shaped recess in the screw; a second shaft unit axially movable and rotatable relative to the first shaft unit and having a transverse edge at its inner end corresponding to and drivingly engageable in a slot on the outer end of the sleeve; a first handle unit attached to the outer end of the first shaft unit, the handle being coupled to the screw as the screw-threaded tip of the first shaft unit is threadedly engaged in the screw-threaded bore of the screw, whereby the screw is movable axially with axial movement of the first-handle unit, and whereby the screw is rotatable with rotational motion of the first handle unit; a second handle unit attached to the outer end of the second shaft unit, the second handle unit being coupled to the sleeve as the transverse edge at the inner end of the second shaft unit is positioned within the slot on the outer end of the sleeve, whereby the sleeve is rotatable and axially movable with respective rotation and axial motion of the second handle unit; and a force-receptive element integral to the first shaft unit and a force applying member drivingly engageable with the force-receptive element to move at least one of the first and second shaft units axially with respect to each.

A still further aspect of the present invention is directed to an improved screwdriver used during surgery for re-joining two pieces of a fractured bone in cooperation with the above-described connector plate, and screw-and-sleeve assembly. The screwdriver comprises: a first shaft unit with engaging means at its inner end for engaging the first shaft unit with the screw to move the screw axially and to rotate the screw; a second shaft unit axially movable and rotatable relative to the first shaft unit and having rotation means at its inner end for rotating the sleeve; and a force-receptive element integral to the first shaft unit and a force applying member drivingly engageable with the force-receptive element to move at least one of the first and second shaft units axially with respect to each.

One other aspect of the present invention is directed to a method for operating a screwdriver in connection with surgery for re-joining two pieces of a fractured bone in cooperation with the above-described connector plate, and screw-and-sleeve assembly. The screwdriver includes first and second shaft units axially and rotatably movable relative to each other. The method of operating the screwdriver comprises: engaging an inner end of the first shaft unit with the screw; engaging an inner end of the second shaft unit with the sleeve; and moving the first shaft unit to effect axial outward movement of the screw relative to the sleeve so that the outer end of the screw passes out of the sleeve and is accommodated within the second shaft unit at a position such that the inner end of the screw protrudes inwardly from the inner end of the sleeve by a length such that the threaded outer end of the sleeve can be threadedly engaged with the bore of the connector plate before the screw is driven to have the inner end of the screw initially bite into the bone beyond the pre-drilled portion.

Still another aspect of the present invention is directed to a method for operating a screwdriver in connection with surgery for re-joining two pieces of a fractured bone in cooperation with the above-described connector plate, and screw-and-sleeve assembly. The screwdriver includes first and second shaft units axially and rotatably movable relative to each other, and a force-receptive element integral to the first shaft unit and a force applying member drivingly engageable with the force-receptive element to move at least one of the first and second shaft units axially with respect to each. The method of operating the screwdriver comprises: engaging an inner end of the first shaft unit with the screw; engaging an inner end of the second shaft unit with the sleeve; and actuating the force applying member drivingly engaged with the force-receptive element to move at least one of the first and second shaft units axially with respect to the other.

DETAILED DESCRIPTION OF THE DRAWINGS

The present invention provides a feature which enables screw II to be retracted into the outer shaft of the screwdriver. More particularly, with a unique force-applying portion of the screwdriver, the outer end 10b of the screw is pulled into the screwdriver by a distance such that the only part extending inwardly of the inner end 14a of sleeve III is the threaded tip at the inner end 10a of the screw. This can be done for every contemplated screw length because the invention provides the range of controllable motion required to retract and accommodate all such long screws within the length of the screwdriver. In contrast, there is no mechanism provided in the above-mentioned U.S. Pat. No. 5,429,641 patent having the range of motion and capability of pulling the long screw into the screwdriver in this manner. Consequently, a relatively longer portion of the long screw II extends from sleeve III. This gave rise to the above-described drawback of misalignment caused by the screw having to bite into the bone before threaded portion 15 of the sleeve could reach and be screwed into bore 5.

Figure 11:
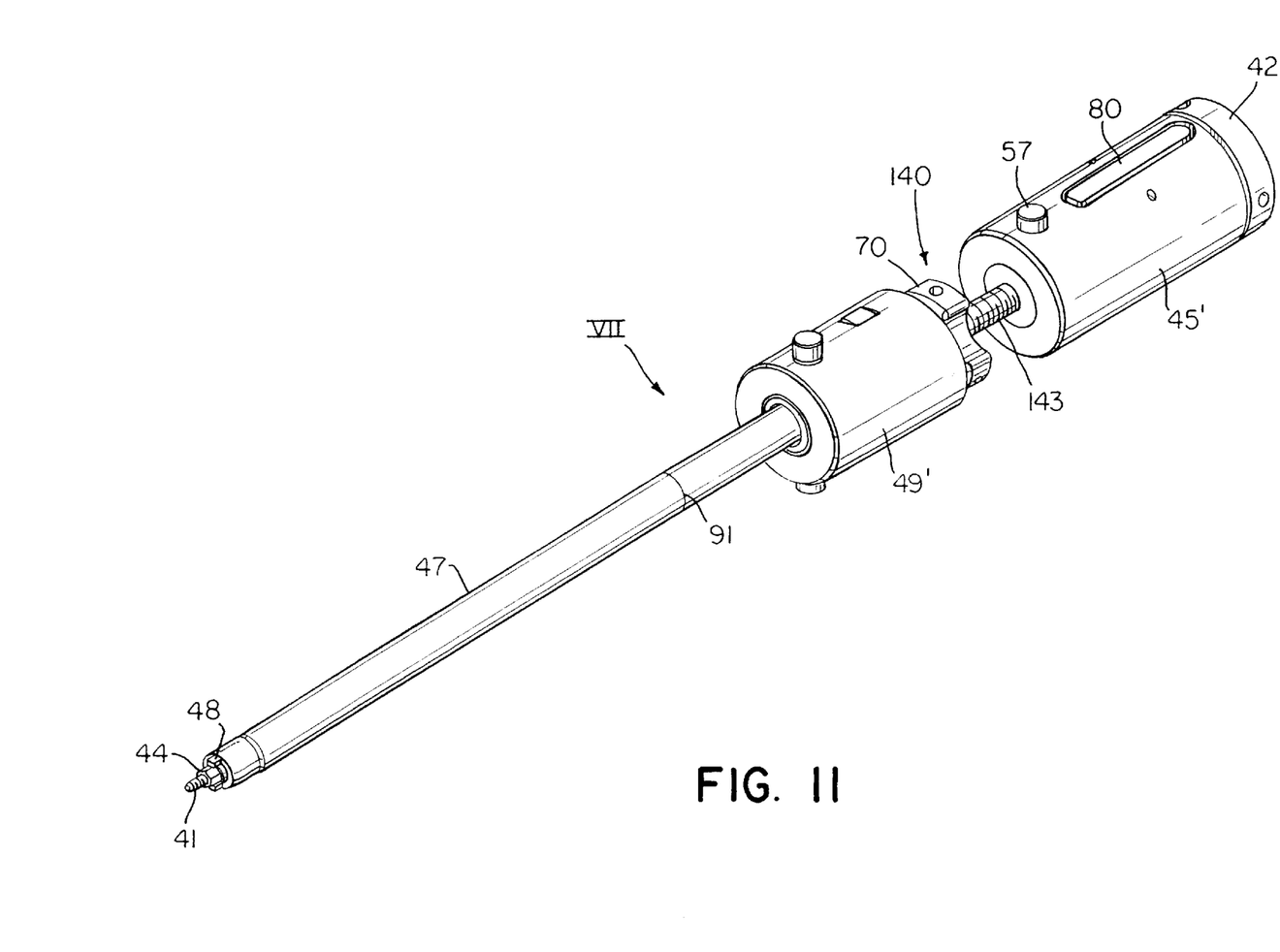
FIG. 11 is a perspective view of an improved scredriver in accordance with the invention.
Figures 12, 12A, 12B:
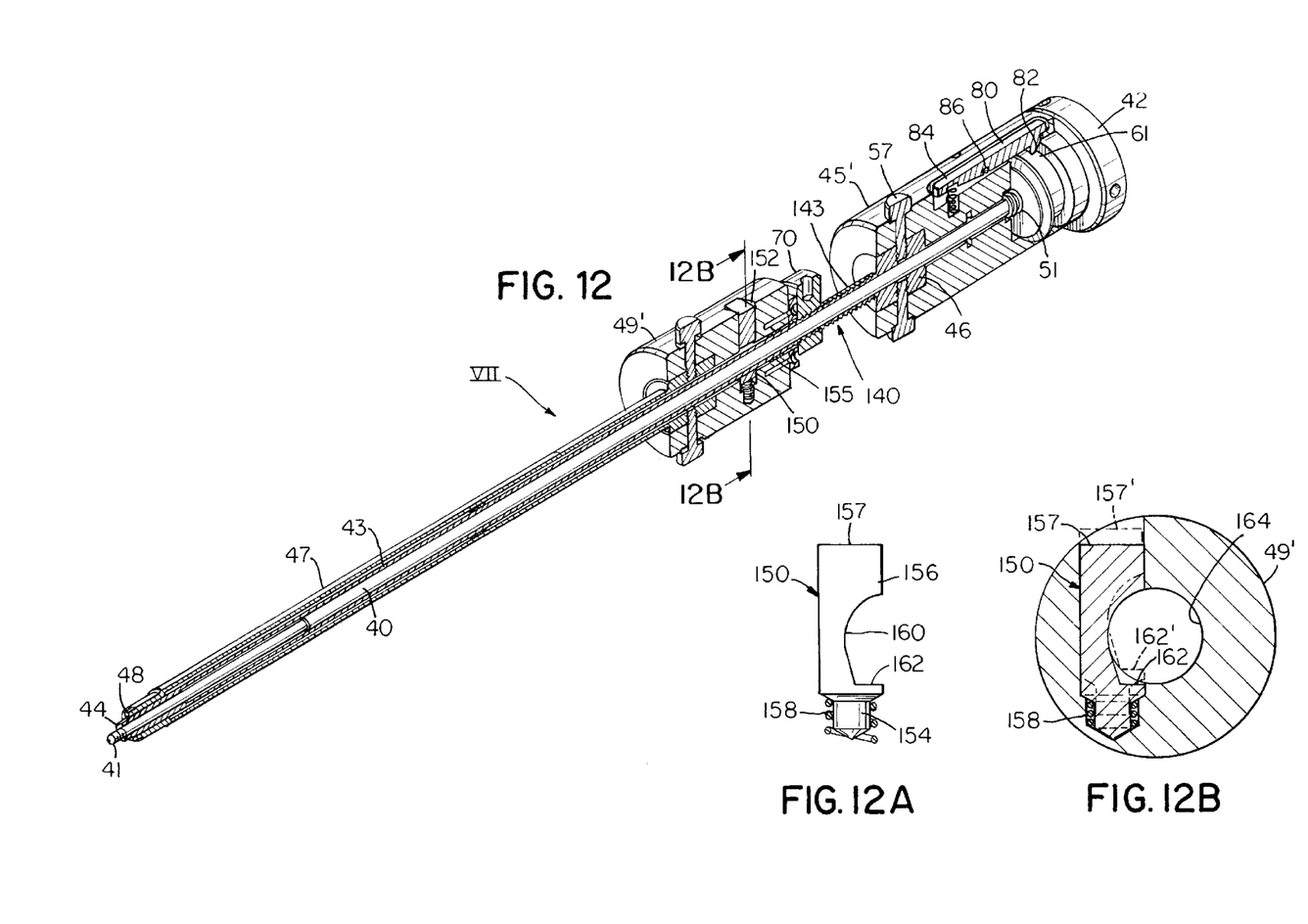
FIG. 12 is longitudinal cross sectional perspective view of the screwdriver shown in FIG. 11.
FIG. 12A is an elevational view of plunger button 150.
FIG. 12B is a cross-section taken along line 12B—12B in FIG. 12.
Figures 13, 14:
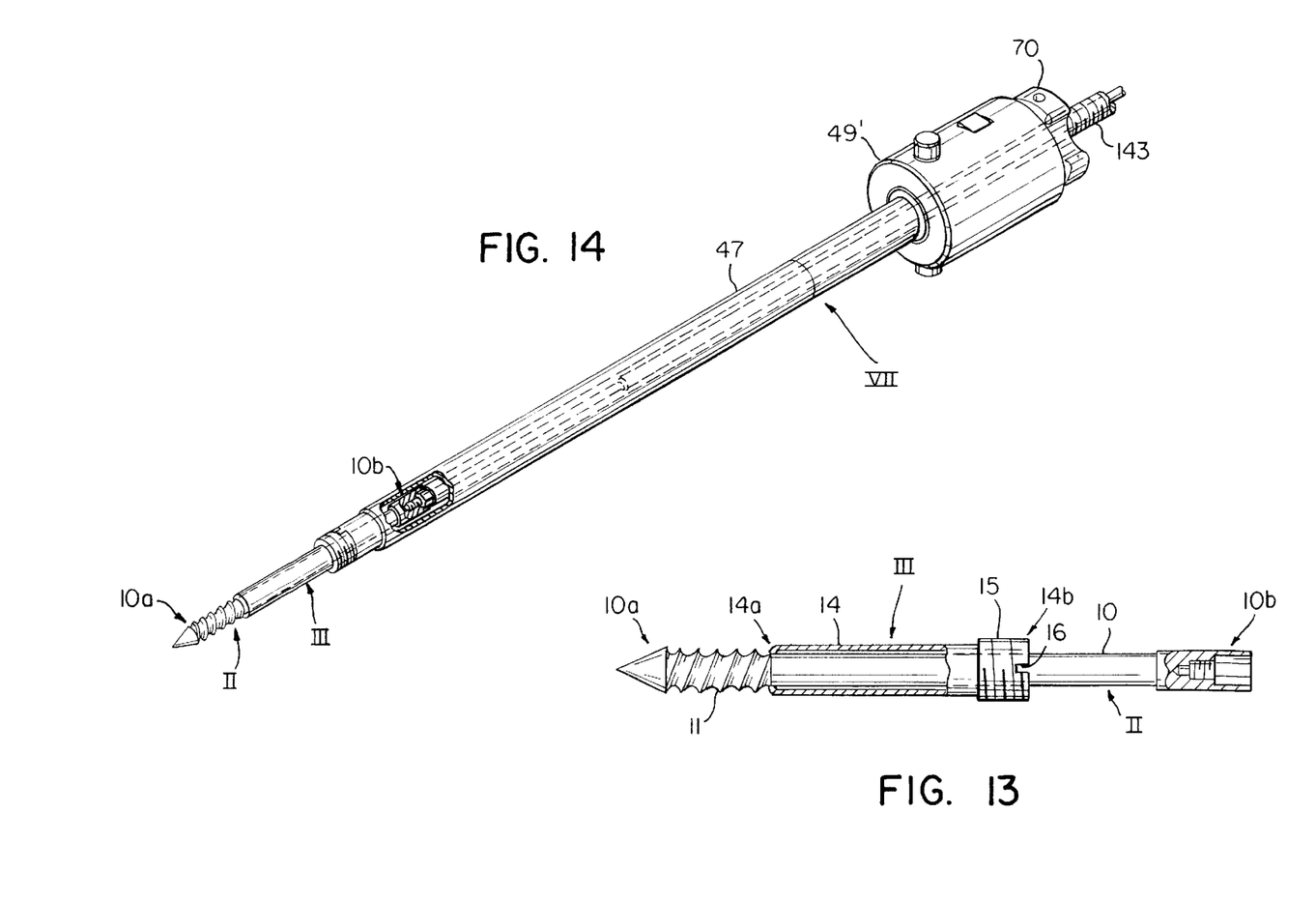
FIG. 13 is a side view and partial sectional view of a screw-and-sleeve assembly, with the screw head extending outwardly of the sleeve.
FIG. 14 is a perspective, partially cut away view of the screwdriver of FIG. 11 fixed to the screw-and-sleeve assembly, with the outer end of the screw received within the screwdriver in accordance with the invention.

The improved screwdriver VII of the invention is illustrated in FIGS. 11, 12 and 14. It comprises the following three concentrically aligned shafts which are independently movable in both axial and rotary directions. Two of the shafts constitute a first shaft unit for engaging and moving the screw II longitudinally and rotationally, whereas the third shaft constitutes a second shaft unit for engaging, rotating and moving the sleeve longitudinally. When a component is the same as its corresponding part in screwdriver V, the same reference numeral is used.

1. An innermost shaft 40 (of the first shaft unit) has a screw-threaded end 41 suitable for engaging the bore 13 in the outer end 10b of the long screw II. Shaft 40 is rotatable and longitudinally movable by a handle 42 at the outer end of the screw driver.

2. An intermediate tubular shaft 43 (of the first shaft unit) has a hexagon-shaped inner end 44 adapted for driving engagement with the hexagonal-shaped recess 12 in the long screw II. Rotation of shaft 43 is used to drive the screw into the bone. Shaft 43 is rotated by cylindrical handle 45' coupled thereto via a disc 46 firmly mounted on the shaft 43.

3. An outermost tubular shaft 47 (of the second shaft unit) has an inner end in the form of cross-wise aligned edges 48 for engagement with slots 16 in the sleeve III. Shaft 47 is rotatable by means of a cylindrical handle 49' for the purpose of screwing sleeves III into the connector plate I.

The above-described components can be axially moved relative to each other, but are urged into their normal position by helical spring 51.

A motion-inducive, or motive, portion 140 is positioned generally between handles 45' and 49'. In particular, an intermediate tubular shaft 43 has an outer portion 143 which is threaded and carries a tapped nut 70 thereon. Threaded portion 143 is a force-receptive member and nut 70 is a force-applying member. The threaded portion 143 is located inwardly of handle 45' and has a length set to accommodate surgical requirements of particular surgeries. For example, such a length can be approximately 130 mm. However, it should be understood that the length can vary greatly depending on the specific surgical operation in which the screwdriver is to be used. Thus, nut 70 and at least a part of threaded portion 143 lie between handles 45' and 49'.

FIG. 13 shows an assembly of the screw and sleeve, with the outer end 10b of screw II being withdrawn well beyond outer end 14b of sleeve III. In fact, the maximum outward motion of screw II is when the crimped inner end 14a of the sleeve comes into engagement with thread 11 at inner end 10a of the screw. The perspective view shown in FIG. 14, partly broken away, shows outer end 10b of the screw retracted into a position considerably within outer shaft 47 of the screwdriver. Thus, with only a relatively small portion of the length of the screw extending beyond the inner end of sleeve III, the distance between threaded portion 15 and the tip of the screw is so short that the threaded portion 15 engages bore 5 before the screw bites into the unpre-drilled bone. Consequently, the above-described possibility of misalignment caused as the screw is deflected after it bites into the bone does not occur. Thus, threaded portion 15 will reliably screw into tapped bore 5 without any difficulty.

Operation of the invention will now be described in a narrative form, to be followed with a step-by-step form.

After the bone has been pre-drilled in alignment with the oblique bores 26, the inner tubular guide 32a is removed in the same manner as described above. Then, two screw-and-sleeve assemblies are inserted and fastened, one after the other, with the aid of the screwdriver VII, as follows.

A long screw II is retracted into its sleeve III to its outer end. The hexagon-shaped end 44 of the screwdriver is pushed into the correspondingly shaped recess 12 in the outer screw end 10b. By rotating handle 42 and pushing it against the force of helical spring 51, the threaded end 41 of the innermost shaft 40 of the screw-driver is screwed into screw-threaded bore 13 of the screw. The protruding edges 48 of the outermost tubular shaft 47 are urged into slots 16 in the end of sleeve III by means of tapped nut 70 which is manually turned to move it inwardly along threaded portion 143 of shaft 43 until it abuts handle 49'. Further turning of nut 70 will retract screw II into the outermost tubular shaft 47 until stopped when crimped inner end 14a of the sleeve comes into contact with thread 11 at the inner end 10a of the screw.

By means of the screwdriver VII, the screw-and-sleeve assembly is pushed in an inward direction through the outer tubular guide 31. With rotation of handle 49' the sleeve is 20 rotated as far as the screw-thread 15 on the sleeve III allows so that the sleeve is screwed into bore 5 of the connector plate. By manually turning nut 70 to move it outwardly away from handle 49' along threaded portion 143 of shaft 43, handle 45' which is connected to the inner shaft 43 by means of collar 46, can then be moved in an inward direction, thereby pushing shaft 43 inwardly. By rotating and pushing handle 45 inwardly, screw II is moved relative to sleeve III.

More specifically, screw II travels through sleeve body 14 as threaded inner end 10a is moved longitudinally toward the femoral head portion (also referred to herein as the femur head). The threaded inner end 10a passes through the pre-drilled bore in the femur bone and then bites into the unpre-drilled bone, utilizing self-cutting edges provided at inner end 10a, as handle 451 is turned manually by the surgeon.

Rotation of handle 45' is stopped as soon as the screw II has reached the required depth in the femur head as viewed by X-ray equipment, or whenever step 17 on the screw (see FIG. 3) reaches the crimped inner end 14b of the sleeve. A pin 82 of a rockable handle 80 is engaged within a circumferential groove 61 and limits the distance to which handle 42 can be moved in an outward direction, while being urged there by spring 51. In addition, during fracture compression (as explained below) pin 82 transfers the load from handle 45' to shaft 40 via handle 42. When inner end 84 of handle 80 is depressed, the handle rocks about point 86 and pin 82 swings clear of the groove 61. This feature enables dismantling of innermost shaft 40 out of intermediate shaft 43 so that both can be cleaned.

In order to pull the fractured head in the direction of the femur shaft and, thus, to compress the fracture, the nut 70, which is in threaded engagement with threaded portion 143 on tubular shaft 43, is turned to advance it inwardly until it bears against handle 49'. With further rotation of the nut 70 while it is in abutment against handle 49', which is locked in place by virtue of its being coupled to the connector plate via outer shaft 47 and sleeve III, shaft 43 is driven outwardly. This moves handle 45' in the same direction which thereby also moves handle 42 outwardly via the releasing handle 80. Outward motion of handle 42 is applied to innermost shaft 40 attached thereto, thus pulling screw II outwardly into the sleeve by means of screw 41 on shaft 40 engaging the tapped bore 13 in the screw end. Such outward motion of the screw compresses the fracture.

After insertion and fixation of the first screw, the second screw is inserted into the fractured bone parts in the same manner.

In operation, the following steps are performed in sequence:

1. Turn nut 70 to move it all the way toward the outer handle 45' so that the hexagonally-shaped end 44 of shaft 43 protrudes beyond outer shaft 47 in order to engage it with recess 12 in the outer end 10b of the screw.
2. Position the screwdriver to engage its hexagonally-shaped end 44 into the hexagonally-shaped recess 12 in the screw. Note that the screw can be held in a customized jig (not shown) to have its outer end protruding therefrom.
3. Push down on the end of the outer handle 42 and turn it clockwise, applying gentle pressure while turning in order to engage threaded end 41 in the screw-threaded bore 13 of the screw.
4. Slide the inner handle 49' inward until the protrusions 48 of the screwdriver fit in slots 16 of the sleeve. Also, such motion will slide sleeve III until its crimped inner end 14a comes into engagement with thread 11 at inner end 10a of the screw. Lock components in position by turning the nut 70 to move it inwardly all the way toward the inner handle 49' until tight. In this position, all of long screw II is accommodated within shaft 47 of screwdriver VII, as shown in FIG. 14, except for the threaded inner end 10a.
5. Push the locked assembly through the outer guide tube 31. When the line 91 on the screwdriver shaft reaches the outer end of the outer guide tube 31, it indicates that the threads of the sleeve are entering the tapped hole 5 in the connector plate I. This is a key point because it is performed before the long screw II bites into the pre-drilled bone (although it is already within the pre-drilled hole). As discussed above in connection with the U.S. Pat. No. 5,429,641 patent, this step is problematic if it were performed only after the screw bites into the bone because that sometimes causes the threaded rear end of the sleeve to become slightly misaligned with the tapped hole in the plate, which the present invention seeks to avoid. Inner handle 49' continues to be turned until the sleeve III is screwed completely into the connector plate.

6. To drive the screw, first turn the nut 70 until it moves all the way outward to the outer handle 45'. This unlocks shaft 43 from its locked position relative to handle 49' so that shaft 43 can be moved inward relative to shaft 47. The outer handle 45' is then turned clockwise to drive the screw as its threaded tip bites into the bone. Rotation of handle 45' continues until the X-ray image shows that the screw is positioned in the subchondral bone.

7. To compress the fracture, turn the nut 70 to move it inwardly to abut against handle 49'. Thereafter, further turning of nut 70 forces shaft 43 and screw II to move outwardly until. This is continued until the upper fracture edge is seen in the X-ray image to move sufficiently toward the lower fracture edge, and the fracture line is closed.

8. When the screw is properly positioned with the previously-described steps, disengage the screw 41 by turning handle 42 counterclockwise.

It is to be noted that if the inner handle 49' is not secured to the screwdriver, care must be taken when loading (engaging) the screw and when disconnecting the screwdriver from the screw since the inner handle 49' may slip off and then would need to be re-sterilized during the operation. In order to prevent this occurrence, a plunger button 150 is provided within a recess 152 in the inner handle 49', as shown in FIGS. 12, 12A, 12B. Plunger button 150 has a narrow shaft 154 and a main body 156. Spring 158 biases button 150 upwardly (as shown in FIG. 12B). A ring stop 155 is fastened to intermediate shaft 43. When the top 157 of button 150 is pushed downward against spring 158, the button is lowered and remains down as long as force is being applied.

The main body 156 of button 150 has an arcuate, laterally facing opening 160 ending with a lower, protruding corner 162. When button 150 is released, it moves upward under force applied by spring 158 so that corner 162 assumes position 162' where it abuts ring stop 155 to prevent corner handle 49' and outermost tubular shaft 47 from slipping off. In this position, top 157 of button 150 extends outside of handle 49' to reach position 157'. When downward force is applied to the top 157 of button 150, main body 156 will be lowered until the arcuate opening 160 is aligned with opening 164 in inner handle 49' with corner 62 no longer being engaged with ring stop 155. Therefore, outermost shaft 47 can be removed for cleaning.

The arrangement of the nut and threaded shaft of the present invention is highly advantageous because it enables the considerable motion that is required for retracting the head of the screws into the screwdriver by a distance such that only a small portion of the screw tip protrudes beyond the inner end of sleeve III. The screwdriver arrangements disclosed in the '641 patent enable only a limited motion in this respect and could not perform such a function for the various lengths of screws that are required to be handled in such a surgical operation.

The preferred embodiment of the screwdriver disclosed herein involves fewer parts than the prior art and, thus, facilitates surgical use and cleaning. In addition, the motive portion 140 is cheaper to manufacture than that of the prior art and, thus, the cost of the screwdriver is reduced.

Although a preferred embodiment of the present invention has been described in detail herein, various modifications thereto will be readily apparent to anyone with ordinary skill in the art. For example, instead of using nut 70 and threaded portion 143, force-applying portion 140 can be implemented as a ratchet mechanism. Also, the first shaft unit has been described as having two components, namely innermost shaft 40 and intermediate shaft 43. However, the functions performed by shafts 40 and 43, namely (a) attachment to the long screw and (2) moving the screw axially and rotationally, could be performed by a single shaft. Thus, the term "first shaft unit" as used herein is intended to cover all implementations of the present invention with such a single shaft configuration capable of accomplishing these functions. All such modifications are intended to be included within the scope of the present invention as defined by the following claims.

What is claimed is:

1. An improved screwdriver for use as part of auxiliary equipment serving to insert and connect a surgical device for percutaneous connection of a fractured upper part of a femur to a femur shaft of a patient, wherein the surgical device comprises the following components to remain in the body of the patient:
  a. a bar-shaped connector plate having an axis, an inner surface to be placed onto the femur, an outer surface, a head portion and a bottom provided with a sharpened end for insertion of said bar-shaped connector plate through a small incision in the skin of the patient, said bar-shaped connector plate being provided in a lower portion thereof with at least two countersunk, through-going bores and in an upper portion thereof with two adjoining oblique, screw-threaded bores directed in an upward direction at an angle of about 130°, a screw-threaded bore perpendicular to the axis of said bar-shaped connector plate being provided in said head portion,
  b. two long screws, each screw having a straight shaft, a wood-screw-shaped inner end for insertion into said fractured upper part of the femur and an outer end coaxially recessed with a polygonal shape, said recess being continued by a screw-threaded bore concentric with an axis of said shaft,
  c. a sleeve of a shorter length than said screw, with the outer end of said screw being positioned in said sleeve in a manner so as to be movable in both axial and rotational directions in the sleeve, the sleeve having an outer end provided with a screw-thread corresponding to the screw thread in said oblique bores in said bar-shaped connector plate such that the sleeve is threadedly engageable within said oblique bores, said sleeve further having at least two recesses for engagement of a screwdriver, and
  d. at least two shorter screws for securing said bar-shaped connector plate to the femur shaft, said at least two shorter screws extending through said countersunk, through-going bores into bone material of the femur shaft;

wherein the auxiliary equipment comprises:
  a. an angular connector arm including a short horizontal portion for connection to the head portion of said bar-shaped connector plate and a longer vertical portion extending parallel to the lower portion of said bar-shaped connector plate, wherein said horizontal portion is provided with an axial perforation for passage of a screw engaging with said screw-threaded bore in said head portion of said bar-shaped connector plate and is shaped to conform to the shape of said head portion to ensure absolute parallelism of said vertical portion with said bar-shaped connector plate, and wherein said vertical portion is provided with two adjoining obliquely directed bores coaxially aligned with said two oblique screw-threaded bores in said plate, and with at least two straight bores coaxially aligned with said at least two countersunk, through-going bores in said plate, b. a first tubular guide of an outer diameter cooperating with said oblique bores in said angular connector arm and of an inner diameter corresponding to an outer diameter of said sleeve covering said long screw, of a length compatible with a distance between the respective oblique bores in said plate and said angular connector arm, c. a first removable tube for insertion into said first tubular guide and having a bore with an inner diameter corresponding to an outer diameter of a guide wire to be pushed therethrough into said fractured upper part, d. a second removable tube for insertion into said first tubular guide and having a bore with an inner diameter corresponding to a diameter of a drill to provide a pre-drilled portion of said femur sized to accommodate said sleeve therein;

e. a guide wire to be pushed through the bore in said first removable tube, f. a drill to be inserted into the bone material through the bore in said second removable tube, g. a second tubular guide for insertion into said straight bores in said angular connector arm, of a length compatible with the distance to said bar-shaped connector plate, and of an inner diameter corresponding to an outer diameter of said shorter screws, and h. a screwdriver for insertion and fixation of said long screws, said screwdriver comprising:
(i) an inner shaft provided with a screw-threaded inner end for engagement with said screw-threaded bore in the recessed end of said long screw,
(ii) an intermediate shaft provided with a polygonal inner end for engagement with said polygonal recess in said long screw to drive said long screw into the upper part of the femur by applying rotational and inwardly directed forces so that the wood-screw shaped inner end bites into the upper part of the femur, and
(iii) an outer shaft provided at an inner end thereof with protruding teeth for engagement with said recesses in said sleeve, wherein said screwdriver is provided with means for pulling said long screw in an outward direction relative to said sleeve, all of said inner, intermediate and outer shafts being independently movable in both axial and rotational directions by handles attached to outer ends thereof, and resilient components are provided to adjust axial alignment of said respective shafts relative to each other, wherein the improvement comprises:
(iv) force-applying means for pulling a section of said long screw by said inner shaft engaged therewith into said outer shaft to have only a length of said long screw protruding inwardly of said sleeve such that the screw-thread on the outer end of said sleeve can be threadedly engaged with each one of said screw-threaded oblique bores in the connector plate before the inner end of said long screw is driven to bite into the femur past said pre-drilled portion, and (v) means in said outer shaft to accommodate therein said section of said long screw.

2. The improved screwdriver of claim 1, wherein said sleeve has a crimped inner end, and the length of the screw section pulled within said outer shaft is defined with the wood-screw-shaped inner end of said long screw coming into contact with said crimped inner end of the sleeve.

3. The improved screwdriver of claim 1, wherein the handle of said inner shaft is outward of the handle of the outer shaft, and wherein said force-applying means comprises a threaded portion on the intermediate shaft between said handles of the inner and outer shafts, and a tapped member is movably engageable on said threaded portion for movement into abutment with at least said handle of the outer shaft.

4. The improved screwdriver of claim 3, wherein said handle of the intermediate shaft is between the handles of the inner and outer shafts, and the threaded portion on the intermediate shaft is inward of said handle of the intermediate shaft.

5. The improved screwdriver of claim 4, wherein said tapped member is movable between said handles of the outer and intermediate shafts.

6. The improved screw driver of claim 5, further comprising a coupling member between said handles of the inner and intermediate shafts so that outward motion of the handle of said intermediate shaft moves the handle of said inner shaft outwardly.

7. The improved screwdriver of claim 6, wherein said coupling member enables resilient inward movement of the handle of said inner shaft relative to said handle of the intermediate shaft.

8. The improved screwdriver of claim 7, wherein said tapped member is a nut.

9. The improved screwdriver of claim 8, wherein the handle of the outer shaft is axially movable over said threaded portion of the intermediate shaft.

10. A screwdriver used during surgery for re-joining two pieces of a fractured bone in cooperation with a connector plate adapted to be secured to a first one of said two bone pieces, the connector plate having at least one screw-threaded bore with its axis being directed at a second of said bone pieces through a pre-drilled portion of the first bone piece, a screw having a screw-shaped inner end for, as the screw is driven with forceful rotation, initially biting into the bone upon passing through the bore of the connector plate and out of the pre-drilled portion of the first bone piece, said screw having an outer end adapted to be engaged with the screwdriver, a sleeve of a shorter length than the screw and being axially movable and rotatable on the screw, the sleeve having an outer end provided with a screw thread corresponding to the screw thread in said bore of the connector plate for threaded engagement therewith, the screwdriver comprising:

a first shaft unit with engaging means at its inner end for engaging the first shaft unit with said screw to move the screw axially and to rotate the screw;

a second shaft unit axially movable and rotatable relative to said first shaft unit and having rotation means at its inner end for rotating said sleeve;

motive means for effecting axial movement of said first shaft unit for moving the screw engaged therewith outward relative to the sleeve so that the outer end of the screw passes through the sleeve and into the second shaft unit to a position therein such that the inner end of said screw protrudes inwardly from the inner end of said sleeve by a length such that the threaded outer end of said sleeve can be threadedly engaged with said bore of the connector plate before the screw is driven to have the inner end of said screw initially bite into said bone beyond the pre-drilled portion.

11. The screwdriver of claim 10, wherein said first shaft unit comprises an inner shaft and a tubular intermediate shaft axially movable and rotatable on the inner shaft, wherein said engaging means of the first shaft unit comprises fixing means on the inner end of said inner shaft for moving said screw axially, and rotating means on the inner end of said intermediate shaft for rotating said screw so that the screw bites into the bone.

12. The screwdriver of claim 11, wherein said fixing means on the inner end of the inner shaft comprises a screw-threaded tip corresponding to and threadedly engageable with a screw-threaded bore in the outer end of said screw.

13. The screwdriver of claim 12, wherein said rotating means on the inner end of the intermediate shaft is polygon-shaped corresponding to a polygon-shaped recess in the outer end of said screw which is coaxial and outward of said screw-threaded bore in the outer end of said screw.

14. The screwdriver of claim 13, wherein said rotation means on the inner end of the second shaft unit comprises a transverse edge corresponding to and drivingly engageable within a slot on the outer end of said sleeve.

15. The screwdriver of claim 14, wherein said motive means comprises a force-receptive element on said first shaft unit and a force-applying member drivingly engageable with said force-receptive element to move said first and second shaft units axially with respect to each other.

16. The screwdriver of claim 15, wherein said force-receptive element comprises a threaded portion and said force-applying member comprises a tapped nut threadedly engaged on said threaded portion.

17. The screwdriver of claim 16, wherein said nut is rotatable in one direction so as to be movable inwardly into abutment against a handle fixed to the outer end of said second shaft unit, whereby further such rotation of said nut in the one direction moves the first shaft unit outwardly relative to the second shaft unit to pull the screw outwardly relative to the sleeve so the screw reaches said position within the second shaft unit.

18. The screwdriver of claim 17, wherein said threaded portion of the force-receptive element is on the intermediate shaft and extends inwardly of a handle fixed to an outer end of said intermediate shaft.

19. The screwdriver of claim 18, wherein said nut is movable between said handles respectively fixed to outer ends of said intermediate shaft and said second shaft unit.

20. The screwdriver of claim 19, further comprising a handle fixed to an outer end of said inner shaft and positioned outwardly of said handle fixed to the intermediate shaft, and coupling means therebetween for moving said handle of the inner shaft outward with outward movement of the handle of said intermediate shaft.

21. The screwdriver of claim 20, wherein said coupling means enables inward motion of the inner shaft handle relative to the handle of said intermediate shaft.

22. The screwdriver of claim 21, wherein said coupling means is resilient for urging the handle of the inner shaft outward relative to the handle of the intermediate shaft.

23. The screwdriver of claim 22, wherein said engaging means of the first shaft unit releasably secures the outer end of said screw to the first shaft unit.

24. The screwdriver of claim 23, wherein said second shaft unit comprises an outer tubular shaft axially movable and rotatable on said intermediate shaft.

25. The screwdriver of claim 24, wherein the rotation means of the second shaft unit engages the outer end of said sleeve.

26. The screwdriver of claim 25, wherein said motive means effects axial movement of said first shaft unit while the sleeve is engaged by said second shaft unit for moving the screw outward relative to the sleeve to reach said position in the second shaft unit.

27. The screwdriver of claim 26, wherein said position of the screw in the second shaft unit is reached when said motive means moves the screw axially outward until a crimped inner end of said sleeve abuts against the screw-shaped inner end of said screw.

28. The screwdriver according to claim 27, wherein the handle of the outer shaft is located inward of the handle on the intermediate shaft.

29. The screwdriver of claim 10, wherein said second shaft unit is sized in length and diameter to accommodate said screw being at said position.

30. The screwdriver of claim 10, wherein said rotation means on the second shaft unit also effects axial motion of said sleeve.

31. The screwdriver of claim 10, wherein said motive means comprises a force-receptive element on said first shaft unit and a force-applying member drivingly engageable with said force-receptive element to move said first and second shaft units axialy with respect to each other.

32. The screwdriver of claim 31, wherein said force-receptive element comprises a threaded portion and said force-applying member comprises a tapped nut threadedly engaged on said threaded portion.

33. The screwdriver of claim 32, wherein said threaded portion extends inwardly of a handle attached to an outer end of said first shaft unit.

34. The screwdriver of claim 33, wherein said second shaft unit comprises a handle fixed to an outer end thereof, and said nut is movable between said handles respectively attached to the first and second shaft units.

35. The screwdriver of claim 10, wherein said engaging means of the first shaft unit releasably secures the outer end of said screw to the first shaft unit.

36. The screwdriver of claim 11, wherein said second shaft unit comprises an outer tubular shaft axially movable and rotatable on said intermediate shaft.

37. The screwdriver of claim 10, wherein the rotation means of the second shaft unit engages the outer end of said sleeve.

38. The screwdriver of claim 10, wherein said motive means effects axial movement of said first shaft unit while the sleeve is engaged by said second shaft unit for moving the screw outward relative to the sleeve to reach said position in the second shaft unit.

39. The screwdriver of claim 10, wherein said position of the screw in the second shaft unit is reached when said motive means moves the screw axially outward until a crimped end of said sleeve abuts against the screw-shaped inner end of said screw.

40. A screwdriver used during surgery for re-joining two pieces of a fractured bone in cooperation with a connector plate adapted to be secured to a first one of said two bone pieces, the connector plate having at least one screw-threaded bore with its axis being directed at a second of said bone pieces through a pre-drilled portion of the first bone piece, a screw having a screw-shaped inner end for, as the screw is driven with forceful rotation, initially biting into the bone upon passing through the bore of the connector plate and out of the pre-drilled portion of the first bone piece, said screw having an outer end adapted to be engaged with the screwdriver, a sleeve of a shorter length than the screw and being axially movable and rotatable on the screw, the sleeve having an outer end provided with a screw thread corresponding to the screw thread in said bore of the connector plate for threaded engagement therewith, the screwdriver comprising:

a first shaft unit having a screw-threaded tip at its inner end corresponding to a screw-threaded bore in said screw for threaded engagement therewith, said first shaft unit further comprising a polygon-shaped portion at its inner end corresponding to and drivingly engageable in a polygon-shaped recess in said screw;

a second shaft unit axially movable and rotatable relative to said first shaft unit and having a transverse edge at its inner end corresponding to and drivingly engageable in a slot on the outer end of said sleeve;

a first handle unit attached to the outer end of said first shaft unit, said first handle unit being coupled to said screw as the screw-threaded tip of the first shaft unit is threadedly engaged in said screw-threaded bore of said screw, whereby the screw is movable axially with axial movement of the first handle unit, and whereby the screw is rotatable with rotational motion of the first handle unit; and a second handle unit attached to the outer end of said second shaft unit, said second handle unit being coupled to said sleeve as the transverse edge at the inner end of the second shaft unit is positioned within said slot on the outer end of said sleeve, whereby the sleeve is rotatable and axially movable with respective rotation and axial motion of said second handle unit;

said second shaft unit being sized to accommodate therein a portion of the screw which is defined by moving the screw outward relative to the sleeve so that the outer end of the screw passes through the sleeve and into the second shaft unit to a position therein such that the inner end of said screw protrudes inwardly from the inner end of said sleeve by only a length such that the threaded outer end of said sleeve can be threadedly engaged with said bore of the connector plate before the screw is driven to have the inner end of said screw initially bite into said bone beyond the pre-drilled portion.

41. The screwdriver of claim 40, wherein said first shaft unit comprises an inner shaft and a tubular intermediate shaft axially movable and rotatable on the inner shaft, wherein said screw-threaded tip at the inner end of said first shaft unit is at the inner end of said inner shaft, and the polygon-shaped portion is at the inner end of said intermediate shaft.

42. The screwdriver of claim 41, wherein said first handle unit comprises a handle attached to the inner shaft and coupled to a handle attached to the intermediate shaft.

43. The screwdriver of claim 42, wherein the portion of said screw accommodated within said second shaft unit is such that a crimped inner end of said sleeve abuts against the screw-shaped inner end of said screw.

44. The screwdriver of claim 40, wherein said second shaft unit is an outer tubular shaft axially movable and rotatable on said first shaft unit, and sized in length and diameter to accommodate therein said portion of the screw.

45. A screwdriver used during surgery for re-joining two pieces of a fractured bone in cooperation with a connector plate adapted to be secured to a first one of said two bone pieces, the connector plate having at least one screw-threaded bore with its axis being directed at a second of said bone pieces through a pre-drilled portion of the first bone piece, a screw having a screw-shaped inner end for, as the screw is driven with forceful rotation, initially biting into the bone upon passing through the bore of the connector plate and out of the pre-drilled portion of the first bone piece, said screw having an outer end adapted to be engaged with the screwdriver, a sleeve of a shorter length than the screw and being axially movable and rotatable on the screw, the sleeve having an outer end provided with a screw thread corresponding to the screw thread in said bore of the connector plate for threaded engagement therewith, the screwdriver comprising:

a first shaft unit having a screw-threaded tip at its inner end corresponding to a screw-threaded bore in said screw for threaded engagement therewith, said first shaft unit further comprising a polygon-shaped portion at its inner end corresponding to and drivingly engageable in a polygon-shaped recess in said screw;

a second shaft unit axially movable and rotatable relative to said first shaft unit and having a transverse edge at its inner end corresponding to and drivingly engageable in a slot on the outer end of said sleeve;

a first handle unit attached to the outer end of said first shaft unit, said handle being coupled to said screw as the screw-threaded tip of the first shaft unit is threadedly engaged in said screw-threaded bore of said screw, whereby the screw is movable axially with axial movement of the first handle unit, and whereby the screw is rotatable with rotational motion of the first handle unit;

a second handle unit attached to the outer end of said second shaft unit, said second handle unit being coupled to said sleeve as the transverse edge at the inner end of the second shaft unit is positioned within said slot on the outer end of said sleeve, whereby the sleeve is rotatable and axially movable with respective rotation and axial motion of said second handle unit; and a force-receptive element integral to said first shaft unit and a force applying member drivingly engageable with said force-receptive element to move at least one of said first and second shaft units axially with respect to each.

46. The screwdriver of claim 45, wherein said force-receptive element comprises a threaded portion and said force-applying member comprises a tapped nut threadedly engaged on said threaded portion.

47. The screwdriver of claim 46, wherein said second shaft unit comprises a tubular outer shaft axially movable and rotatable on said first shaft unit, including on said threaded portion of said first shaft unit.

48. The screwdriver of claim 47, wherein said second handle unit is positioned inwardly of said first handle unit, and said nut being movable between said first and second handle units.

49. The screwdriver of claim 48, wherein said first shaft unit comprises an inner shaft and a tubular intermediate shaft axially movable and rotatable on the inner shaft, wherein said screw-threaded tip at the inner end of said first shaft unit is at the inner end of said inner shaft, and the polygon-shaped portion is at the inner end of said intermediate shaft, said first handle unit comprising one handle attached to an outer end of said inner shaft and coupled to another handle attached to an outer end of said intermediate shaft, said one handle being positioned outwardly of said other handle, and said threaded portion being on the intermediate shaft and extending inwardly from said other handle.

50. A screwdriver used during surgery for re-joining two pieces of a fractured bone in cooperation with a connector plate adapted to be secured to a first one of said two bone pieces, the connector plate having at least one screw-threaded bore with its axis being directed at a second of said bone pieces through a pre-drilled portion of the first bone piece, a screw having a screw-shaped inner end for, as the screw is driven with forceful rotation, initially biting into the bone upon passing through the bore of the connector plate and out of the pre-drilled portion of the first bone piece, said screw having an outer end adapted to be engaged with the screwdriver, a sleeve of a shorter length than the screw and being axially movable and rotatable on the screw, the sleeve having an outer end provided with a screw thread corresponding to the screw thread in said bore of the connector plate for threaded engagement therewith, the screwdriver comprising:

a first shaft unit with engaging means at its inner end for engaging the first shaft unit with said screw to move the screw axially and to rotate the screw;

a second shaft unit axially movable and rotatable relative to said first shaft unit and having rotation means at its inner end for rotating said sleeve; and a force-receptive element integral to said first shaft unit and a force applying member drivingly engageable with said force-receptive receptive element to move at least one of said first and second shaft units axially with respect to each.

51. The screwdriver of claim 50, wherein said force-receptive element comprises a threaded portion and said force-applying member comprises a tapped nut threadedly engaged on said threaded portion.

52. The screwdriver of claim 51, wherein said second shaft unit comprises a tubular outer shaft axially movable and rotatable on said first shaft unit, including a threaded portion of said first shaft unit.

53. The screwdriver of claim 52, wherein said first shaft unit includes a first handle unit and said outer shaft includes a second handle unit positioned inwardly of said first handle unit, and said nut being movable between said first and second handle units.

54. The screwdriver of claim 53, wherein said first shaft unit comprises a n inner shaft and a tubular intermediate shaft axially movable and rotatable on the inner s haft, wherein said screw-threaded tip at the inner end of said first shaft unit is at the inner end of said inner shaft, and the polygon-shaped portion is at the inner end of said intermediate shaft, said first handle unit comprising one handle attached to an outer end of said inner shaft and coupled to another handle attached to an outer end of said intermediate shaft, said one handle being positioned outwardly of said other handle, and said threaded portion being on the intermediate shaft and extending inwardly from said other handle.

55. A method for operating a screwdriver in connection with surgery for re-joining two pieces of a fractured bone in cooperation with a connector plate adapted to be secured to a first one of said two bone pieces, the connector plate having at least one screw-threaded bore with its axis being directed at a second of said bone pieces through a pre-drilled portion of the first bone piece, a screw having a screw-shaped inner end for, as the screw is driven with forceful rotation, initially biting into the bone upon passing through the bore of the connector plate and out of the pre-drilled portion of the first bone piece, the screw having an outer end adapted to be engaged with the screwdriver, a sleeve of a shorter length than the screw and being axially movable and rotatable on the screw, the sleeve having an outer end provided with a screw thread corresponding to the screw thread in said bore of the connector plate for threaded engagement therewith, the screwdriver having first and second shaft units axially and rotatably movable relative to each other, the method of operating the screwdriver comprising:

engaging an inner end of the first shaft unit with said screw;

engaging an inner end of said second shaft unit with said sleeve;

moving said first shaft unit to effect axial outward movement of the screw relative to the sleeve so that the outer end of the screw passes out of the sleeve and is accommodated within the second shaft unit at a position such that the inner end of said screw protrudes inwardly from the inner end of said sleeve by a length such that the threaded outer end of said sleeve can be threadedly engaged with said bore of the connector plate before the screw is driven to have the inner end of said screw initially bite into said bone beyond the pre-drilled portion.

56. The method of claim 50, further comprising manipulating the second shaft unit to threadedly engage the outer end of the sleeve with the screw thread in said bore of the connector plate, and then manipulating the first shaft unit to move the screw inwardly from said position and forcefully rotate said screw to bite into said bone beyond the pre-drilled portion.

57. A method for operating a screwdriver in connection with surgery for re-joining two pieces of a fractured bone in cooperation with a connector plate adapted to be secured to a first one of said two bone pieces, the connector plate having at least one screw-threaded bore with its axis being directed at a second of said bone pieces through a pre-drilled portion of the first bone piece, a screw having a screw-shaped inner end for, as the screw is driven with forceful rotation, initially biting into the bone upon passing through the bore of the connector plate and out of the pre-drilled portion of the first bone piece, the screw having an outer end adapted to be engaged with the screwdriver, a sleeve of a shorter length than the screw and being axially movable and rotatable on the screw, the sleeve having an outer end provided with a screw thread corresponding to the screw thread in said bore of the connector plate for threaded engagement therewith, the screwdriver having first and second shaft units axially and rotatably movable relative to each other, and a force-receptive element integral to said first shaft unit and a force applying member drivingly engageable with said force receptive element to move at least one of said first and second shaft units axially with respect to each, the method of operating the screwdriver comprising:

engaging an inner end of the first shaft unit with said screw;

engaging an inner end of said second shaft unit with said sleeve;

actuating the force applying member drivingly engaged with the force-receptive element to move at least one of the first and second shaft units axially with respect to the other.

58. The method of claim 57, wherein said force-receptive element comprises a threaded portion and said force-applying member comprises a tapped nut threadedly engaged on said threaded portion, the method further comprising:

rotating said nut in one direction so as to move it inwardly into abutment against a handle attached to the outer end of said second shaft unit, whereby further such rotation of said nut in the one direction moves the first shaft unit outwardly relative to the second shaft unit to pull the screw outwardly relative to the sleeve.

* * * * *